(12) United States Patent
Ju et al.

(10) Patent No.: US 10,538,794 B2
(45) Date of Patent: Jan. 21, 2020

(54) OLIGOSACCHARIDE LIBRARIES AND METHODS OF PRODUCTION

(71) Applicant: Emory University, Atlanta, GA (US)

(72) Inventors: Tongzhong Ju, Atlanta, GA (US); Richard Cummings, Boston, MA (US); Matthew Kudelka, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/826,387

(22) Filed: Nov. 29, 2017

(65) Prior Publication Data

US 2018/0148755 A1    May 31, 2018

Related U.S. Application Data

(60) Provisional application No. 62/427,649, filed on Nov. 29, 2016.

(51) Int. Cl.
*C12P 19/04* (2006.01)
*C40B 50/00* (2006.01)

(52) U.S. Cl.
CPC ................... *C12P 19/04* (2013.01)

(58) Field of Classification Search
None
See application file for complete search history.

(56) References Cited

U.S. PATENT DOCUMENTS

| | | | |
|---|---|---|---|
| 6,994,966 B2 | 2/2006 | Dukler | |
| 7,572,592 B2 | 8/2009 | Dotan | |
| 7,608,414 B2 | 10/2009 | Dotan | |
| 7,772,192 B2 * | 8/2010 | Esko | C07H 13/04 514/25 |
| 8,129,128 B2 | 3/2012 | Dotan | |
| 8,232,073 B2 | 7/2012 | Crawford | |
| 9,222,120 B2 | 12/2015 | Crawford | |
| 2010/0166726 A1 * | 7/2010 | Campbell | A61K 31/085 424/94.5 |
| 2013/0034557 A1 | 2/2013 | Nishimura | |
| 2014/0274771 A1 * | 9/2014 | Elizazu | G01N 33/54353 506/9 |
| 2015/0083906 A1 | 3/2015 | Mehmet | |

FOREIGN PATENT DOCUMENTS

| | | | | |
|---|---|---|---|---|
| EP | 2358760 | 2/2015 | | |
| WO | 2010118347 | 10/2010 | | |
| WO | WO-2010118347 A2 * | 10/2010 | ............ | A61K 31/716 |
| WO | 2013158585 | 10/2013 | | |

OTHER PUBLICATIONS

Kudelka et al., Cellular O-Glycome Reporter/Amplification to Explore O-Glycans of Living Cells, Nature Methods, 2015, 13(1), 81-88. (Year: 2015).*

Kudelka et al., Simple Sugars to Complex Disease—Mucin-Type O-Glycans in Cancer, HHS Public Access, Author Manuscript, 2015, 1-65. (Year: 2015).*
Delannoy et al., Benzyl-N-Acetyl-alpha-D-Galactosaminide Inhibits the Sialylation and the Secretion of Mucins by a Mucin Secreting HT-29 Cell Subpopulation, Glycoconjugate Journal, 1996, 13, 717-726. (Year: 1996).*
Song et al., Novel Strategy to Release and Tag N-Glycans for Functional Glycomics, Bioconjugate Chemistry, 2014, 25, 1881-1887. (Year: 2014).*
Karkkainen et al., Iodine-Mediated Glycosylation en route to Mucin-Related Glyco-Aminoacids and Glycopeptides, Carbohydrate Research, 2008, 343, 1830-1834. (Year: 2008).*
Pouilly et al., Metabolic Glycoengineering Through the Mammalian GalNAc Salvage Pathway, The FEBS Journal, 2012, 279, 586-598. (Year: 2012).*
Brockhausen et al. The Separation by Liquid Chromatography (Under Elevated Pressure) of Phenyl, Benzyl, and o-Nitrophenyl Glycosides of Oligosaccharides, Carbohydrate Research, 120 (1983) 3-16.
Delannoy et al. Benzyl-N-acetyl-a-o-galactosaminide inhibits the sialylation and the secretion of mucins by a mucin secreting HT-29 cell subpopulation, Glycoconjugate Journal (1996) 13: 717-726.
Gross et al. Optically Pure N-substituted Derivatives of Benzyl 2-Amino-2-deoxy-alpha- and-beta-D-glucopyranoside, J. Org. Chem., 1967, 32 (9), pp. 2759-2763.
Jensen et al. Mucin-type O-glycosylation—putting the pieces together, FEBS Journal 277 (2010) 81-94.
Karkkainen et al. Iodine-mediated glycosylation en route to mucin-related glyco-aminoacids and glycopeptides, Carbohydrate Research 343 (2008) 1830-1834.
Kuan et al. Inhibition of Mucin Glycosylation by Aryl-N-acetyl-alpha-galactosaminides in Human Colon Cancer Cells, J Biol Chem. 1989, 264(32):19271-7.
Kudelka et al. Cellular O-Glycome Reporter/Amplification to explore O-glycans of living cells, Nat Methods. 2016,13 (1):81-6.
Lebrilla et al. The prospects of glycan biomarkers for the diagnosis of diseases, Mol. BioSyst., 2009, 5, 17-20.
Pouilly et al. Metabolic glycoengineering through the mammalian GalNAc salvage pathway, FEBS Journal 279 (2012)586-598.
Roth et al. Identification and Quantification of Protein Glycosylation, International Journal of Carbohydrate Chemistry vol. 2012, Article ID 640923, 10 pages.
Sarkar et al. Disaccharide uptake and priming in animal cells: Inhibition of sialyl Lewis X by acetylated Gal beta 1 to 4GLcNAcbeta-O-naphthalenemethanol, Proc. Natl. Acad. Sci. USA vol. 92, pp. 3323-3327, 1995.

(Continued)

*Primary Examiner* — Amy M Bunker
(74) *Attorney, Agent, or Firm* — Emory Patent Group

(57) ABSTRACT

This disclosure relates to libraries of oligosaccharides comprising multiple individual oligosaccharides derived from cells that contain a tag or detectable marker. In certain embodiments, the tag or detectable marker is an oxygen linked to the oligosaccharides through the first carbon of a sugar ring. In certain embodiments, the disclosure relates to methods of generating the libraries of oligosaccharides using saccharides, e.g., monosaccharides, or a disaccharide, in which hydroxyl groups are chemically acetylated.

7 Claims, 8 Drawing Sheets

(56) References Cited

OTHER PUBLICATIONS

Song et al. Novel Strategy to Release and Tag N-Glycans for Functional Glycomics, Bioconjugate Chem., 2014, 25 (10), pp. 1881-1887.

Thermo Scientific, Guide to Glycan Analysis, 2013, available at www.thermoscientific.com.

Xolin et al. Glycosylation with N-acetyl glycosamine donors using catalytic iron(III) triflate: from microwave batch chemistry to a scalable continuous-flow process, Org. Chem. Front, 2014, 1, 992-1000.

Zanetta et al. Massive in vitro synthesis of tagged oligosaccharides in 1-benzyl-2-acetamido-2-deoxy-alpha-D-galactopyranoside treated HT-29 cells, Glycobiology. 2000,10(6):565-75.

\* cited by examiner

US 10,538,794 B2

OLIGOSACCHARIDE LIBRARIES AND METHODS OF PRODUCTION

CROSS-REFERENCE TO RELATED APPLICATIONS

This application claims the benefit of U.S. Provisional Application No. 62/427,649 filed Nov. 29, 2016. The entirety of this application is hereby incorporated by reference for all purposes.

STATEMENT REGARDING FEDERALLY SPONSORED RESEARCH

This invention was made with government support under Grant 5U01CA168930 awarded by the National Institutes of Health. The government has certain rights in the invention.

BACKGROUND

Protein glycosylation is a common post-translational modification in all animals that creates post-genomic diversity, but systems-level approaches for glycomics are lacking in most biological settings. A primary need is simple and sensitive technology that can be used to analyze multiple glycans synthesized by cells (the cellular glycome). This type of analysis has been challenging because of the diversity and complexity of glycans, the low abundance of certain glycan species, the poor sensitivity of existing glycomics approaches, and the lack of efficient and unbiased strategies for releasing glycans from complex samples. Current technologies for evaluating glycans require relatively large amounts of biological samples for detailed structural analyses, which limits their widespread application.

One of the most common types of protein glycosylation is mucin-type O-glycosylation (R-GalNAc-α-O-Ser or -Thr), where R represents extended structures, which is present on the majority of proteins that traverse the secretory apparatus and is important in many normal and pathologic settings. Nonetheless, little is known about either the repertoire of O-glycans or how specific O-glycan structures regulate biology, largely because of a lack of effective technologies for O-glycomics. In contrast to N-glycans, which can be released enzymatically, O-glycans require chemical strategies for their release—primarily alkaline β-elimination, which is inefficient, is potentially biased, and may result in O-glycan degradation via peeling reaction. Thus, there is a need to identify improved methods for evaluating O-glycans in living cells.

Brockhausen et al report in vitro N-acetylglucosaminyl-transferase (GlcNAc-transferase) activities using synthetic oligosaccharide alpha-O-glycosides, i.e., GalNAc-α-O—R, as GlcNAc substrates, wherein R is phenyl (Ph), benzyl (Bn), or o-nitrophenyl (ONP) instead of a peptide. Carbohydrate Research, 1983, 120, 3-16. Sarkar et al. report the inhibition of sialyl Lewis X by acetylated Gal(beta)1-4GlcNAc(beta)-O-naphthalenemethanol. Proc. Natl. Acad. Sci. USA, 1995, 92:3323-3327.

Kuan et al. report that aryl-N-acetyl-alpha-galactosaminides can be useful for the structural and functional studies of mucin macromolecules and other O-linked glycoproteins. J Biol Chem, 1989, 264(32):19271-7. See also Delannoy et al. Benzyl-N-acetyl-alpha-D-galactosaminide inhibits the sialylation and the secretion of mucins by a mucin secreting HT-29 cell subpopulation. Glycoconj. J. 13, 717-726 (1996) and Zanetta, et al. Massive in vitro synthesis of tagged oligosaccharides in 1-benzyl-2-acetamido-2-deoxy-alpha-D-galactopyranoside treated HT-29 cells. Glycobiology 10, 565-575 (2000).

Kudelka et al. report cellular O-glycome reporter/amplification to explore O-glycans of living cells. Nat Methods, 2016, 13(1):81-6.

References cited herein are not an admission of prior art.

SUMMARY

This disclosure relates to libraries of oligosaccharides comprising multiple individual oligosaccharides derived from cells that contain a tag or detectable marker. In certain embodiments, the tag or detectable marker is oxygen linked to the oligosaccharides through the first carbon of a sugar ring. In certain embodiments, the disclosure relates to methods of generating libraries of oligosaccharides using saccharides, e.g., monosaccharides, or a disaccharide, in which hydroxyl groups are chemically acetylated.

In certain embodiments, the disclosure relates to methods comprising, providing a saccharide wherein the first carbon of the sugar ring is linked to through oxygen to a tag or detectable marker and hydroxyl groups in the monosaccharide are substituted with acetyl groups to provide an acetylated tagged oxygen linked saccharide and mixing the acetylated tagged oxygen linked saccharide with a cell under conditions such that the acetylated tagged oxygen linked saccharide penetrates into the cell and under conditions such that the saccharide is converted into oxygen linked oligosaccharides or multiple tagged oxygen linked oligosaccharides.

In certain embodiments, the disclosure relates to methods of creating a library of oligosaccharides comprising, providing a saccharide or monosaccharide wherein the first carbon of the sugar ring is linked to through oxygen to a tag or detectable marker which is not a peptide, such as an aromatic molecule or a hydrophobic molecule, and wherein hydroxyl groups in the saccharide or monosaccharide are substituted with acetyl groups to provide an acetylated tagged oxygen linked saccharide or monosaccharide; mixing the acetylated tagged oxygen linked saccharide or monosaccharide with a cell under conditions such that the acetylated linked saccharide or monosaccharide penetrates into the cell under conditions such that the saccharide or monosaccharide is converted into oxygen linked oligosaccharides or multiple tagged oxygen linked oligosaccharides; and separating the oxygen linked oligosaccharides or multiple tagged oxygen linked oligosaccharides to provide to provide a library of oligosaccharides comprising purified individual tagged oxygen linked oligosaccharides.

In certain embodiments, the disclosure relates to methods comprising, providing a saccharide wherein the first carbon of the sugar ring is linked to through oxygen to a tag or detectable marker and hydroxyl groups in the monosaccharide are substituted with acetyl groups to provide an acetylated tagged oxygen linked saccharide and inserting the acetylated tagged oxygen linked saccharide into a cell under conditions such that the saccharide is converted into oxygen linked oligosaccharides or multiple tagged oxygen linked oligosaccharides.

In certain embodiments, the disclosure relates to methods of creating a library of oligosaccharides comprising, providing a saccharide or monosaccharide wherein the first carbon of the sugar ring is linked to through oxygen to a tag or detectable marker which is not a peptide, such as an aromatic molecule or a hydrophobic molecule, and wherein hydroxyl groups in the saccharide or monosaccharide are substituted with acetyl groups to provide an acetylated tagged oxygen linked saccharide or monosaccharide; inserting the acetylated tagged oxygen linked saccharide or monosaccharide into a cell under conditions such that the saccharide or monosaccharide is converted into oxygen linked oligosaccharides or multiple tagged oxygen linked oligosaccharides; and separating the oxygen linked oligosaccharides or multiple tagged oxygen linked oligosaccharides to provide to provide a library of oligosaccharides comprising purified individual tagged oxygen linked oligosaccharides.

In certain embodiments, the disclosure relates to compositions and methods for determining binding of undefined or unknown mixtures of oligosaccharides that are tagged, separated by chromatographic means, and printed on microarrays for interrogation with entities that bind to predetermined saccharide constructs. Typically, once a positive binding event is identified to a particular undefined or unknown tagged oxygen linked oligosaccharide on the microarray, that oligosaccharide is then sequenced after recovery from the tagged library, i.e., without a starting knowledge about the structure of an oligosaccharide in a mixture, the oligosaccharide in the mixture or sample can be identified by its binding to an entity in combination with other mass spectroscopic information.

In certain embodiments, the disclosure contemplates placing the purified individual tagged oxygen linked oligosaccharides in a plurality of zones, wells, or areas.

In certain embodiments, the disclosure relates to oxygen linked oligosaccharides or multiple tagged oxygen linked oligosaccharides conjugated or non-specifically absorbed to a solid surface e.g., glass slide, a bead, polymer, metal, or silicon wafer.

In certain embodiments, the disclosure contemplates that the saccharides are monosaccharides or disaccharides. In certain embodiments, contemplated monosaccharide and disaccharides contain D-Glucose, D-Galactose, D-Galactose, L-Galactose, D-Mannose, D-Allose, L-Altrose, D-Gulose, L-Idose, D-Talose, D-Ribose, D-Arabinose, L-Arabinose, D-Xylose, D-Lyxose, D-Erythrose, D-Threose, L-glycero-D-manno-Heptose, D-glycero-D-manno-Heptose, 6-Deoxy-L-altrose, 6-Deoxy-D-talose, D-Fucose, L-Fucose, D-Rhamnose, L-Rhamnose, D-Quinovose, 2-Deoxyglucose, 2-Deoxyribose, D-Glucosamine, D-Galactosamine, D-Mannosamine, D-Allosamine, L-Altrosamine, D-Gulosamine, L-Idosamine, D-Talosamine, N-Acetyl-D-glucosamine, N-Acetyl-D-galactosamine, N-Acetyl-D-mannosamine, N-Acetyl-D-allosamine, N-Acetyl-L-altrosamine, N-Acetyl-D-gulosamine, N-Acetyl-L-idosamine, N-Acetyl-D-talosamine, N-Acetyl-D-fucosamine, N-Acetyl-L-fucosamine, N-Acetyl-L-rhamnosamine, N-Acetyl-D-quinovosamine, Apiose, Bacillosamine, Thevetose, Acofriose, or combinations thereof.

In certain embodiments, the disclosure contemplates that all of the hydroxyl groups of the saccharides, monosaccharides, or oligosaccharides are acetylated, or optionally all except one hydroxyl group are acetylated in a monosaccharide, or optionally all except one hydroxyl group are acetylated per monosaccharide for an oligosaccharide.

In certain embodiments, multiple tagged oxygen linked oligosaccharides are secreted outside the cell. In certain embodiments, the multiple tagged oxygen linked oligosaccharides are obtained in a sample of cellular cytosol. In certain embodiments, the multiple tagged oxygen linked oligosaccharides are obtained by breaking the cell membrane and evaluating the cellular cytosol. In certain embodiments, the multiple tagged oxygen linked oligosaccharides are obtained by penetrating the cell membrane with a device configured to aspirate or otherwise withdraw a cytosol sample, e.g. due to capillary motion, and evaluating the sample cellular cytosol.

In certain embodiments, the methods disclosed herein contemplate permethylation of the oxygen linked oligosaccharides or multiple tagged oxygen linked oligosaccharides or the purified individual tagged oxygen linked oligosaccharides, i.e., converts hydroxyl groups in the oligosaccharides to methoxy groups. In certain embodiments, permethylation comprises the step of substituting hydroxyl groups in the multiple tagged oxygen linked oligosaccharides with methyl. In certain embodiments, permethylation comprising the step of substituting hydroxyl groups in the multiple individual tagged oxygen linked oligosaccharides with methyl. In certain embodiments, substituting hydroxyl groups in the multiple individual tagged oxygen linked oligosaccharides with methyl comprises the step of mixing multiple tagged oxygen linked oligosaccharides or purified individual tagged oxygen linked oligosaccharides with a methylating agent under conditions such that methoxy is formed in place of the alcohol, i.e., hydroxyl group. In certain embodiments, the methylating agent is a halogenated methane such as methyl iodine for mixing methyl iodide in dimethyl sulfoxide solution containing a base, e.g., sodium hydroxide.

In certain embodiments, the tag or detectable marker is an aromatic molecule or other lipophilic molecule. In certain embodiments, the tag or detectable marker has a molecular weight of less than 150, 300, or 600 g/mol. In certain embodiments, the aromatic molecule is benzyl, phenyl, 4-nitrophenyl, naphthyl, or derivatives thereof.

In certain embodiments, separating oligosaccharides is done by chromatography or high pressure liquid chromatography.

In certain embodiments, the methods disclosed herein further comprise analyzing the oligosaccharides by mass spectroscopy to provide measured molecular weights. In certain embodiments, the methods disclosed herein further comprise predicting the structures of oligosaccharides based on the measured molecular weights.

In certain embodiments, the purified individual tagged oxygen linked oligosaccharides are quantified in relation to each other.

In certain embodiments, the purified individual tagged oxygen linked oligosaccharides are arranged on a surface in separate locations.

In certain embodiments, the mixing is done in a media containing the saccharide, monosaccharide, or N-acetyl-D-galactosamine in a concentration of less than 250, 200, 100, or 50 µM.

In certain embodiments, the purified individual tagged linked oligosaccharides are mixed with one or more glycan-binding protein and evaluated to for binding of the purified individual tagged oxygen linked oligosaccharides with one or more glycan-binding protein. In certain embodiments, a pattern of binding of the purified individual tagged oxygen linked oligosaccharides with one or more glycan-binding protein is determined.

In certain embodiments, the disclosure contemplates methods disclosed herein for diagnostic purposes. In certain embodiments, the binding patterns or patterns of purified individual tagged oxygen linked oligosaccharides and quantities are determined to be correlated to a disease or cellular condition. In certain embodiments, the disclosure contemplates using methods disclosed herein to diagnose or monitor a disease or condition in a subject.

In certain embodiments, the disclosure relates to methods comprising measuring one or more tagged oxygen linked oligonucleotides in a sample from a subject using methods disclosed herein to provide a measured value and comparing the measured value to a reference, predetermined, or control value, wherein an increase or decrease of the measured value compared to the reference, predetermined, or control value indicates the presence or absence of a disease or condition in the subject.

In certain embodiments, the disclosure relates to methods of treatment based on diagnosis of subject using methods disclosed herein.

In certain embodiments, the disclosure further comprises exposing the solid surface with zones of immobilized tagged oxygen linked oligonucleotides to an analyte with glycan adhesion properties, e.g., glycan binding protein, antibody, microbes, toxins, a viral strain, virus particle, virus like particle, bacteria, or other pathogen, and evaluating the zones for binding of the analyte, e.g., by evaluating changes of the fluorescence pattern on the solid surface before and after exposure of the zones to the analyte. The analyte may be evaluated in light of its own binding or how the analyte changes the binding of known binders. It is contemplated that the analyte itself may be conjugated to a fluorescent molecule or fluorescence quenching molecule to the tagged molecule on the immobilized tagged oxygen linked oligonucleotides to allow for FRET.

In certain embodiments, the compositions and methods disclosed herein may be used to identify carbohydrate structures in tagged oxygen linked oligonucleotides associated with human disorders and diseases; identify glycan-binding proteins that recognize carbohydrate structures; identify genes regulating expression of tagged oxygen linked oligonucleotides; to identify host-pathogen interactions involving tagged oxygen linked oligonucleotides in viral, microbial, and parasitic diseases; and to identify changes in glycosylation associated with heritable and acquired human genetic disorders, e.g., used for diseases and disorders involving altered tagged oxygen linked oligonucleotides expression, e.g., inheritable diseases, acquired diseases, cancer, IgA nephropathy.

In certain embodiments, the disclosure contemplates methods of diagnosing infections with certain viral strains by creating a tagged oxygen linked oligonucleotides library with compositions disclosed herein and determining the binding patterns of the virus. Comparing the viral recognition pattern of known strains, e.g., influenza H1N1, H3N2 (Sub7-1 or Sub6-1), to the pattern from a sample from a subject one may identify specific viruses, strains, and subtypes.

Analyzing may be done by detecting or measuring changes of light emission or absorption about the location of the tagged oxygen linked oligonucleotides epitope upon binding or other physical phenomena associated with antibody binding. In certain embodiments, the tagged oxygen linked oligonucleotides may be immobilized to a zone on a solid surface, exposed to the sample, e.g., serum, and mixed with a secondary antibody that recognizes the primary antibody. The secondary antibody may contain a marker, e.g., fluorescent molecule. The data from analyzing the binding properties may be recorded in the memory of a computer, displayed on a computer screen, or transmitted by writing or an electronic document to the subject or a medical professional.

In certain embodiments, this disclosure relates to kits comprising a solid surface comprising purified individual tagged oxygen linked oligosaccharides made by the process disclosed herein. In certain embodiments, the disclosure relates to kits comprising compositions disclosed herein and optionally a fluid transfer device in a surrounding or air sealed container.

DETAILED DESCRIPTION

Figure 1:
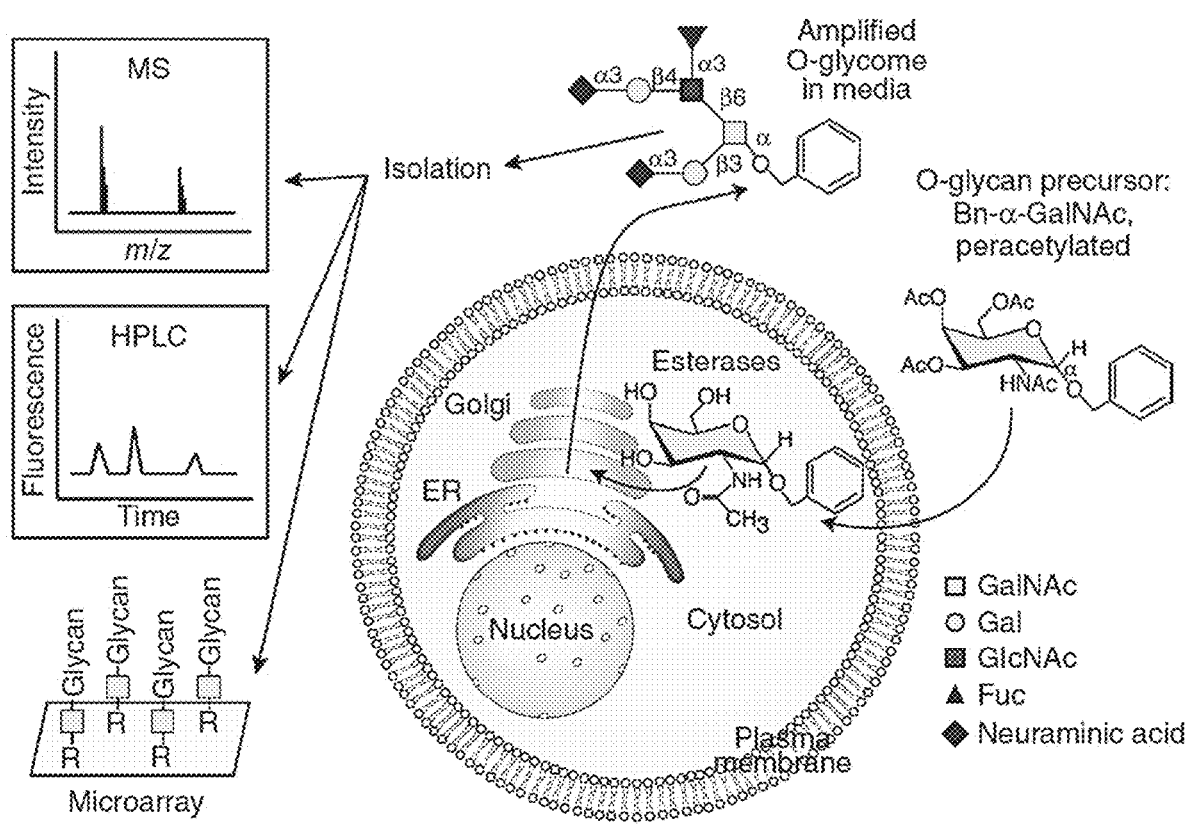
FIG. 1 illustrates a method disclosed herein. Cells are incubated with peracetylated chemical precursor ($Ac_3$GalNAc-alpha-Bn). Although it is not intended that embodiments of this disclosure be limited by any particular mechanism, it is believed that cytosolic esterases generate Bn-alpha-GalNAc, which is taken up in the Golgi and modified by native glycosyltransferases during anterograde transport. Elaborated (in vivo enzymatically produced) Bn-O glycans are secreted into the media, purified and then analyzed by MS or HPLC or printed on glycan microarray for interrogation by glycan-binding proteins. ER, endoplasmic reticulum.
Figure 2A:
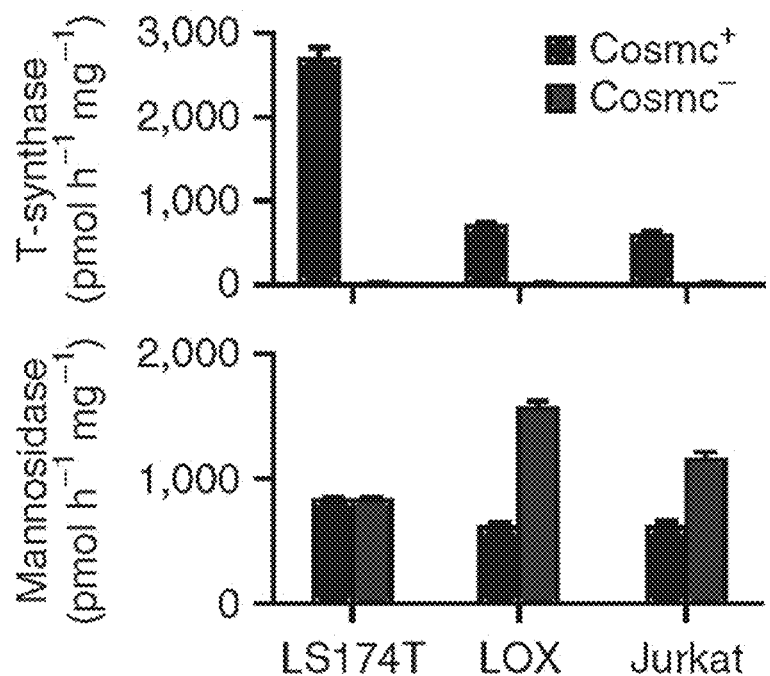
FIG. 2A shows data indicating the chaperone Cosmc and active T-synthase are important for production of core 1- and core 2-based Bn-O-glycans. Activity of T-synthase relative to mannosidase control enzyme for LS174T colorectal cells, LOX melanoma cells and Jurkat T cells with and without functional Cosmc.
Figure 2B:
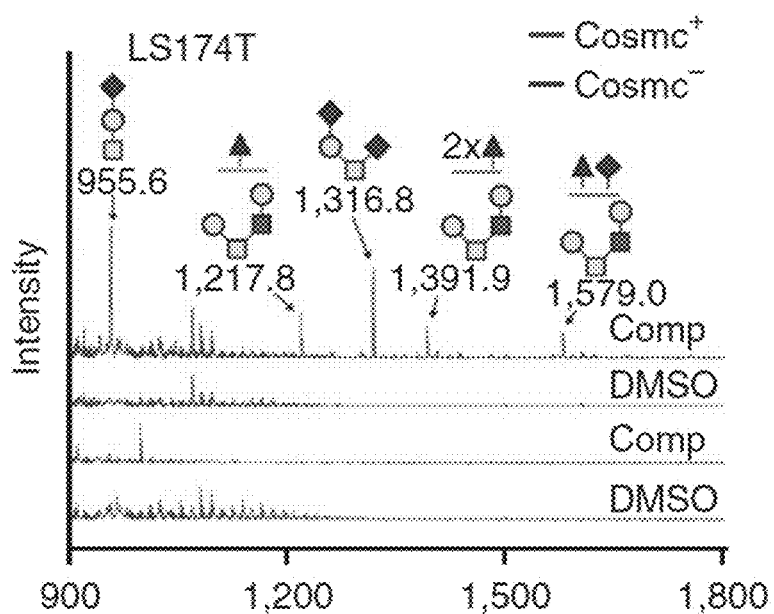
FIG. 2B shows MS data for Bn-O-glycans in media from the same LS174T cells after incubation with 50 μM Ac3GalNAc-alpha-Bn compound (Comp) or vehicle (DMSO) for 3 d. Major glycans are annotated for LS174T for clarity; highly fucosylated minor species were also observed. Spectra are offset but scaled to the same absolute intensity for each cell.
Figure 2C:
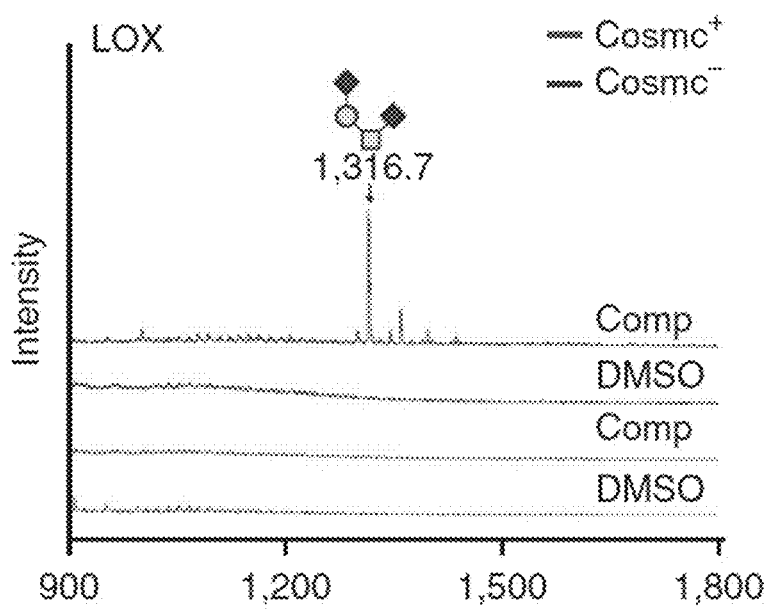
FIG. 2C shows data for LOX cells.
Figure 2D:
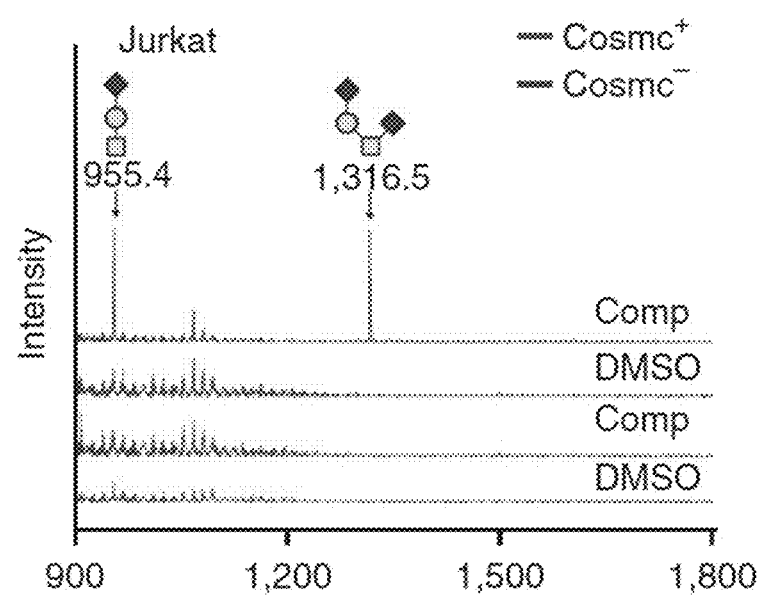
FIG. 2D shows data for Jurkat cells.

To promote an understanding of the principles of the present disclosure, descriptions of specific embodiments of the disclosure follow and specific language is used to describe the specific embodiments. It will nevertheless be understood that no limitation of the scope of the disclosure is intended by the use of specific language. Alterations, further modifications, and such further applications of the principles of the present disclosure discussed are contemplated as would normally occur to one ordinarily skilled in the art to which the disclosure pertains.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

A "subject" refers to any animal such as a human patient, livestock or a domestic pet.

As used herein a "sample" refers to a composition taken from or originating from a subject. Examples of samples include cell samples, blood samples, tissue samples, hair samples, and urine or excrement samples.

As used herein, the term "detectable marker" is used broadly to encompass a variety of types of molecules which are detectable through spectral properties (e.g., fluorescent markers or "fluorophores") or through functional properties (e.g., affinity markers). A representative affinity marker includes biotin, which is a ligand for avidin and streptavidin. An epitope marker is a marker functioning as a binding site for antibody. Since chimeric receptor proteins and antibodies can be produced recombinantly, receptor ligands are effective affinity markers.

As used herein the term "tag" or "tagged" molecule refers to a molecule that will photoluminescence, i.e., emit light as a result of the absorption of photons, e.g., fluorescence or phosphorescence.

An "aromatic" group refers to a molecular ring structure with atoms in a sp2 hybridized state that provide a delocalized conjugated electron system with an even number of delocalized electrons, but not a multiple of 4. As used herein, it is intended to include heterocyclic or non-heterocyclic aromatic groups. The group may have multiple rings and some of the rings may not be aromatic provided at least one ring is aromatic.

"Chromatography" refers to processes used to purify individual components from mixtures by passing a mixture contained in a "mobile phase" through a "stationary phase," which separates the analyte to be measured from other components in the mixture. A "separation medium" refers to the stationary phase or adsorbent. In certain embodiments, the disclosure relates to analysis of samples using chromatographic processes.

Ion exchange chromatography, liquid chromatography, normal-phase (NP) and reversed-phase chromatography (RP), affinity chromatography, and expanded bed adsorption (EBA) chromatograph all use separation mediums. In ion exchange chromatography, the separation medium is typically an ion exchange resin that carries charged functional groups which interact with oppositely charged groups of the compound to be retained. In affinity chromatography, the separation medium is typically a gel matrix, often of agarose, typically coupled with metals or molecules that bind with markers or tags such antigens, antibodies, enzymes, substrates, receptors, and ligands. Methods utilizing antibodies or antigens (epitopes) coupled to the separation medium is typically referred to as immunoaffinity chromatography and the separation medium is referred to as an immunoabsorbant.

Liquid chromatography (LC) is a separation technique in which the mobile phase is a liquid. Typical separation mediums for liquid column chromatography include silica gel, alumina, and cellulose powder. Liquid chromatography carried out under a relatively high pressure is referred to as high performance liquid chromatography (HPLC). HPLC is historically divided into two different sub-classes based on the polarity of the mobile and stationary phases. The technique in which the stationary phase is more polar than the mobile phase (e.g. toluene as the mobile phase, silica as the stationary phase) is called normal phase liquid chromatography (NPLC) and the opposite (e.g. water-methanol mixture as the mobile phase and $C_{18}$=octadecylsilyl as the stationary phase) is called reversed phase liquid chromatography (RPLC).

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Contemplated derivative include switching carbocyclic, aromatic or phenyl rings with heterocyclic rings or switching heterocyclic rings with carbocyclic, aromatic or phenyl rings, typically of the same ring size. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Cellular O-Glycome Reporter/Amplification (CORA) to Explore O-Glycans of Living Cells Cellular O-Glycome Reporter/Amplification (CORA) is a method used to amplify and profile mucin-type O-glycans synthesized by living cells. Cells convert added peracetylated benzyl-α-N-acetylgalactosamine to a large variety of modified O-glycan derivatives that are secreted from cells, allowing for easy purification for analysis by HPLC and mass spectrometry (MS). Relative to conventional O-glycan analyses, CORA typically resulted in an ~100-1,000-fold increase in sensitivity and identified a more complex repertoire of O-glycans in more than a dozen cell types from *Homo sapiens* and *Mus musculus*. Furthermore, when coupled with computational modeling, CORA can be used for predictions about the diversity of the human 0-glycome and offers new opportunities to identify novel glycan biomarkers for human diseases.

CORA is an approach for both amplifying and profiling the mucin-type O-glycome in living cells. Its high sensitivity and amplification enabled us to identify novel complex O-glycans, which were not seen in the β-elimination-released samples, indicating that β-elimination might not provide enough material for MS or MS/MS evaluation of these low-abundance species. For example, MS analyses of β-eliminated O-glycans from WEHI-3 cells have not identified sialyl-LeX on core 2 O-glycans, a critical component on PSGL-1 recognized by P-selectin, which binds WEHI-3 cells. However, this minor structure was previously confirmed by enrichment analysis, and here it was detected by CORA, which directly demonstrates the improved sensitivity of CORA with respect to conventional methods. Thus the novel structures identified are natural O-glycans, mostly present on glycoproteins at low abundance. CORA using Ac$_3$GalNAc-α-Bn is specific for O-glycans, as Cosmc-deficient cells do not produce Bn-O-glycans and culturing cells with the isomer Ac$_3$GlcNAc-β-Bn produced no glycans or a trisaccharide (Sia-Gal-GlcNAc-Bn) only. The latter result suggests that the enzymes responsible for poly-N-acetyl-lactosamine production, I antigen synthesis and α3-fucosylation are relatively specific to extended O-glycans in the cell lines examined.

CORA was effective at low concentrations (less than 250 μM) and short incubation times with no observed effect on cellular properties or glycosylation. Prior studies showed that treatment of cells with high concentrations of Bn-α-GalNAc for O-glycan inhibition produces mainly small Gal-β3-GalNAc-α1-O-Bn and sialyl-Gal-β3-GalNAc-α1-O-Bn derivatives. However, success with CORA using low concentrations of Ac$_3$GalNAc-α-Bn derivative as a precursor indicates that it is readily taken up by live cells, converted to Bn-α-GalNAc, efficiently used by T-synthase and further accessed by a wide range of enzymes in the secretory pathway, including the most terminal types of glycan modifications and extensions. It is noteworthy that this approach defines the global ability of cells to make O-glycans but might not always reflect their natural relative abundances, which can be influenced by the concentration of protein substrates or expression of O-glycosylated polypeptide cores.

This approach could allow for assessment of the diversity and repertoire of O-glycans in an animal O-glycome. Recent studies using transfected CHO cells engineered to express all major O-glycan core structures, along with chemical release techniques, identified ~70 different glycan structures. The repertoire of O-glycans is likely much larger, as there are nearly 1,000 mucin-type O-glycan determinants, with probably <500 nonsulfated O-glycans. In this regard, our computational modeling allowed us to predict the size of the nonsulfated and/or nonphosphorylated animal O-glycome as including ~376 distinct glycan structures.

An advantage of CORA is that live cells are used to generate the O-glycome, but the cells can also be analyzed by conventional techniques afterward if desired for comparative analyses. Advances in cell and organoid culture have enabled culture of many normal and diseased tissue, yet glycan release is often not sufficiently sensitive for analyses of such precious specimens. CORA could enable researchers to address this challenge by allowing amplification of the glycome of these cells in addition to high-throughput analysis of tumor cells. Although we limited our analyses to mucin-type O-glycans, CORA may be a general strategy for amplifying and profiling many classes of glycosylation, with appropriate precursors. Although we used small numbers of cells for glycan analysis, large numbers of cells in continuous culture could also be used as glycan-biosynthesis factories to prepare any and all natural O-glycans, even those difficult to synthesize chemically. Bn-O-glycans or their derivatives could be isolated to generate therapeutic glycans, to test the roles of unusual glycans in cell recognition or growth, or for display in glycan microarrays. Amplification of the O-glycome by CORA is a new paradigm in cellular glycomics that will make new types of investigations possible in a wide range of basic and clinical settings to give new insights into the role of O-glycans in physiology and disease.

EXAMPLES

Cells Take Up Ac3GalNAc-α-O-Bn and Secrete Bn-O-Glycans

Mucin-type O-glycan biosynthesis begins with the transfer of GalNAc to Ser or Thr residues in glycoproteins to generate GalNAc-α1-O-Ser or -Thr (Tn antigen), which T-synthase extends to the dominant core 1 O-glycan Gal-β3-GalNAc-α1-O-Ser or -Thr. To assess the repertoire of glycosyltransferases and glycosylation reactions in the secretory pathway for the O-glycome, a chemical O-glycan precursor, peracetylated benzyl (Bn)-α-GalNAc (Ac3GalNAc-α-Bn), was developed which is taken up by living cells, deacetylated, modified by native glycosyltransferases in the presence of nucleotide sugar donors in the secretory pathway, and then secreted into media (FIG. 1). Bn-α-GalNAc structurally mimics the precursor GalNAc- α1-O-Ser or -Thr (Tn antigen) in O-glycoproteins and was used in vitro as an acceptor for T-synthase and core 3 GnT.

Monosaccharides linked to hydrophobic aglycones can prime glycan biosynthesis. Bn-α-GalNAc at low concentrations could be used as a surrogate acceptor by T-synthase to promote the formation of free Bn-O-glycans representing the cellular O-glycome. Ac3GalNAc-α-Bn, a more hydrophobic derivative of Bn-α-GalNAc, was used to enhance cellular uptake as shown for other peracetylated carbohydrate compounds and predicted that upon entry into cells, Ac3GalNAc-α-Bn would become activated by cytosolic esterases to regenerate Bn-α-GalNAc. Bn-α-GalNAc would then be transported into the secretory pathway, modified by glycosyltransferases and secreted into media as biosynthetic Bn-O-glycans that could be purified and analyzed by MS (FIG. 1).

Adherent (HEK293) and suspension (Molt-4) cells were cultured in complete media containing 50 µM Ac3GalNAc-α-Bn or vehicle (dimethyl sulfoxide (DMSO)) for 3 d. Putative Bn-O-glycans from the media were separated from larger material with a cutoff membrane, purified by C18 chromatography, permethylated and analyzed by MALDI-TOF-MS. Here as elsewhere, the permethylated nonsulfated and/or nonphosphorylated glycans were analyzed. Clean MALDI-TOF profiles were observed with Bn-O-glycan compositions corresponding to core 1- and core 2-based structures from cells cultured with Ac3GalNAc-α-Bn but not from cells cultured with DMSO, indicating efficient uptake and modification of the O-glycan precursor by glycosyltransferases in vivo.

To assess whether peracetylation of Bn-α-GalNAc enhances uptake and subsequent sensitivity, breast cancer cells (MDA-MB-231) were incubated with 0-250 µM Ac3GalNAc-α-Bn or Bn-α-GalNAc for 3 d. Bn-O-glycans with the predicted sialylated core 2 structure were observed at concentrations as low as 25 µM for Ac3GalNAc-α-Bn, but only at the highest concentration of 250 µM for Bn-α-GalNAc. Further, peracetylation of Bn-α-GalNAc was stable in complete media for at least 3 d. Thus, peracetylation improved sensitivity, and at such low concentrations potential side effects should be limited, as explored below.

To optimize conditions, MDA-MB-231 cells were cultured with 0-250 µM Ac3GalNAc-α-Bn for 2-4 d. Bn-O-glycans in culture media were seen at all time points and in culture conditions with as little as 5 µM Ac$_3$GalNAc-α-Bn for 2 d, and their profiles were stable over time. Remarkably, increasing the Ac$_3$GalNAc-α-Bn concentration shifted abundance from disialylated to monosialylated core 2, supporting observations that glycosyltransferase:substrate ratios drive glycan microheterogeneity. Thus, CORA should be performed with low concentrations of Ac$_3$GalNAc-α-Bn. For most subsequent studies, cells were incubated with 50 µM Ac$_3$GalNAc-α-Bn for 3 d. At these conditions, Ac$_3$GalNAc-α-Bn was not toxic to cells, did not alter cellular morphology or granularity and did not alter cell surface 0- or N-glycosylation, and Bn-O-glycans were stable after secretion from cultured cells.

Synthesis of Core 1-Based Bn-O-Glycans Use T-Synthase

CORA was performed on cells with mutant or wild-type C1galt1c1 (Cosmc), a chaperone known to be essential for T-synthase activity. Only cells with functional Cosmc and active T-synthase secreted Bn-O-glycans when we administered Ac$_3$GalNAc-α-Bn (FIG. 2A-D). Furthermore, cells incubated with the isomer Ac$_3$GlcNAc-β-Bn secreted no Bn-O-glycans or only the simple trisaccharide Neu5Ac-Gal-GlcNAc-Bn, indicating that Ac$_3$GalNAc-α-Bn is specific for mucin-type O-glycans.

Accuracy of CORA

O-glycome profiles obtained via CORA were compared to profiles from β-elimination available through the Consortium for Functional Glycomics (CFG) database. WEHI-3 and HL-60 cells were analyzed because they have complex O-glycomes with distinctive structures such as Cad (GalNAc-β1,4-(α2,3-Neu5Ac)Gal-β1,3/4-R) and extended poly-N-acetyl-lactosamines ([3Gal-β1,4-GlcNAc-β1]n) that are challenging to detect by β-elimination of lysates but are observed on purified glycoproteins.

Figure 3A:
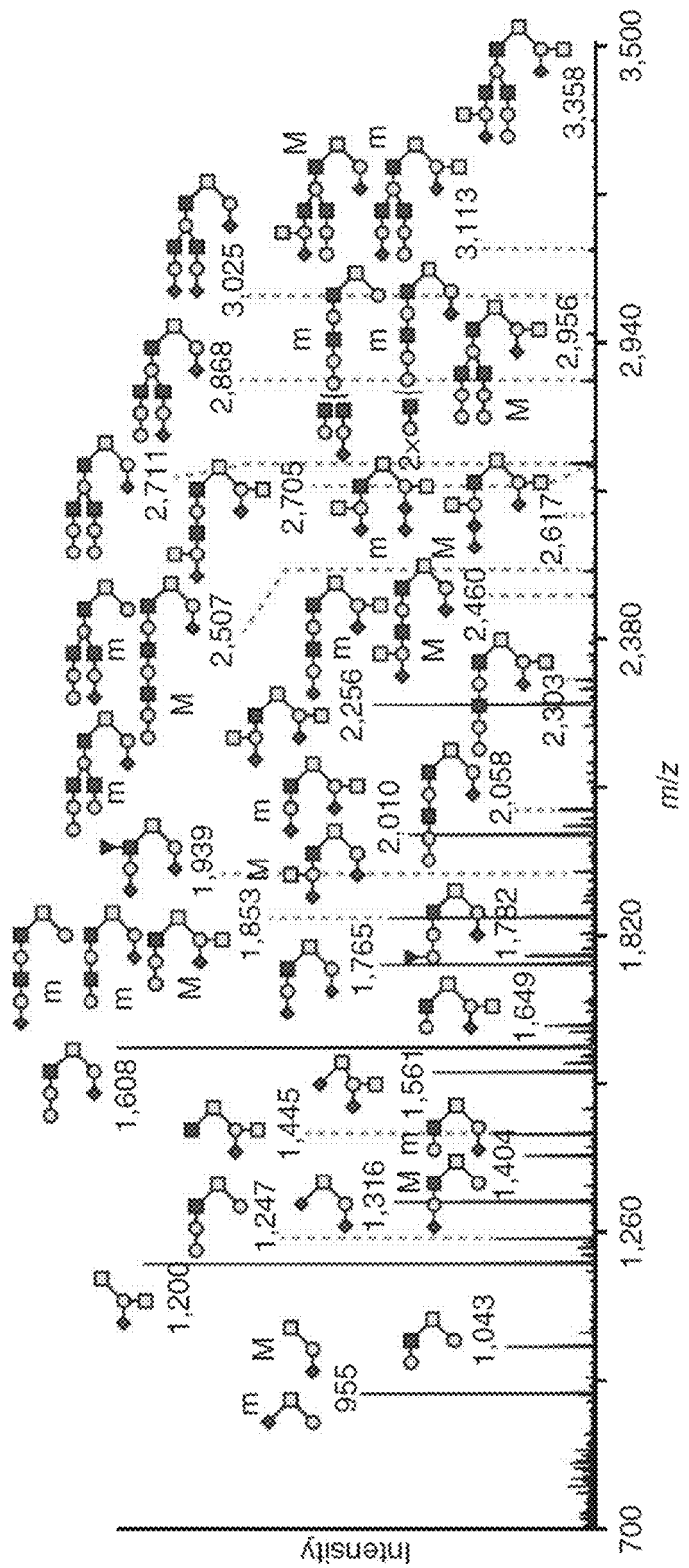
FIG. 3A shows data indicating the accuracy of CORA for profiling the O-glycome. MALDI-TOF-MS characterization of Bn-O-glycans from WEHI-3 cells incubated with 50 μM $Ac_3$GalNAc-α-Bn. Only the nonsulfated and/or nonphosphorylated glycans were analyzed. Putative structures are based on composition, MS/MS and biosynthetic knowledge.
Figure 3B:
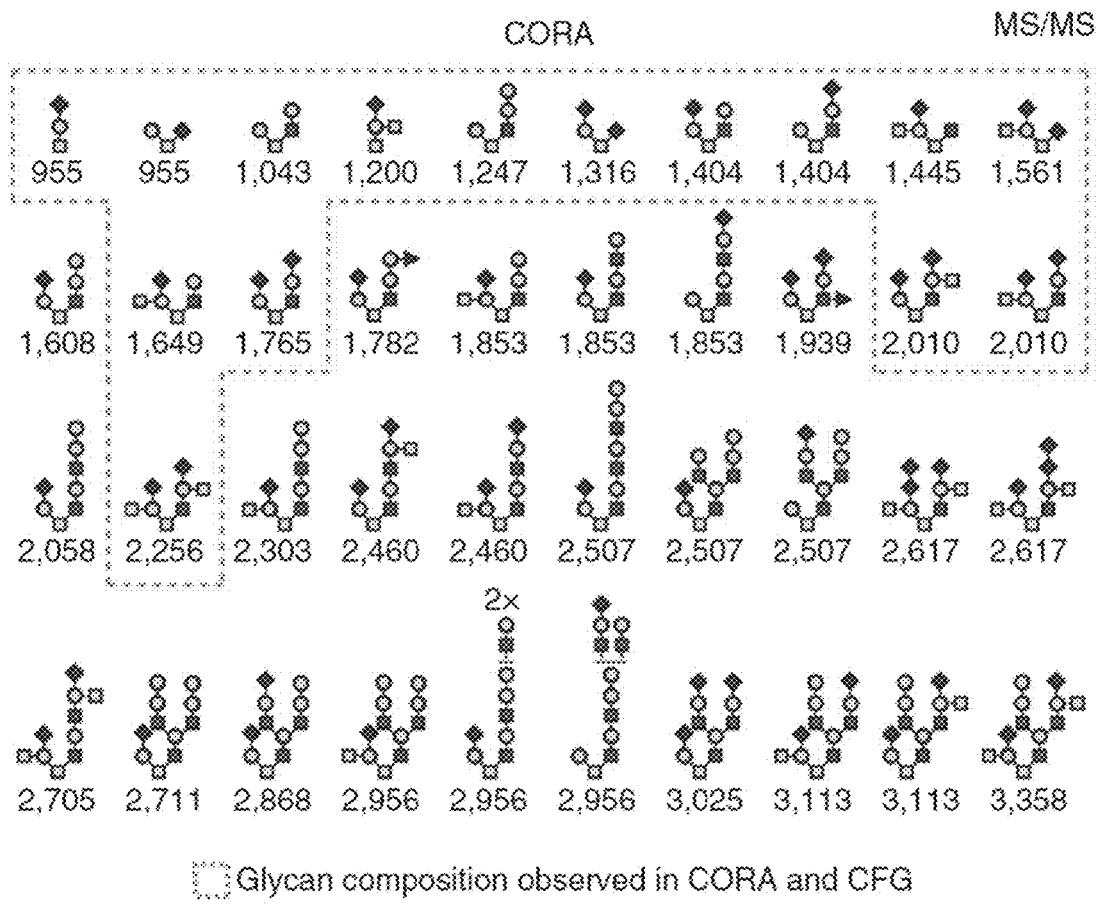
FIG. 3B shows data on Bn-O-glycans from CORA (MS/MS structures) compared to profiles from alkaline β-elimination (dashed outlines indicate glycan compositions observed in both CORA and β-elimination FIG. 3C shows CFG data using MS compositions.
Figure 3C:
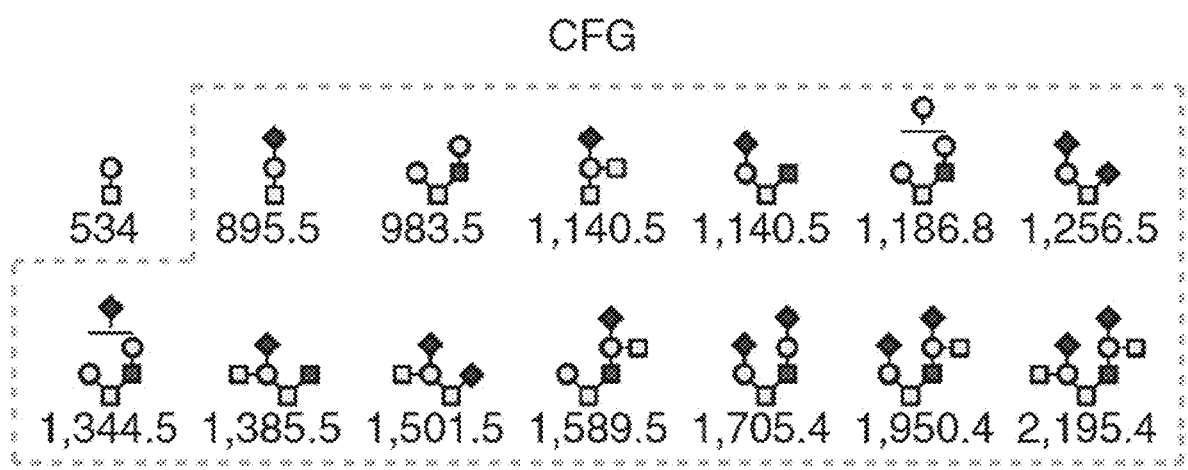
FIG. 3D illustrates the number of glycans (by composition) observed with CORA, β-elimination (CFG data) and both.
Figure 3D:
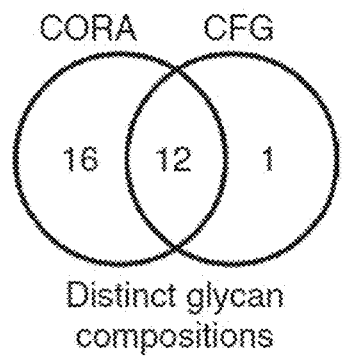

MALDI-TOF-MS and MS/MS profiles showed that WEHI-3 and HL-60 cells produced 40 and 11 glycan structures, respectively, including sialylated core 1- and core 2-based glycans for both cells and Cad antigen in WEHI-3 cells (FIG. 3A). CORA detected most of the compositions seen in β-eliminated samples (12 of 13 for WEHI-3 cells and 4 of 7 for HL-60 cells) as well as many additional compositions (16 for WEHI-3 cells (FIGS. 3B and C) and 6 for HL-60 cells) that were generally the most complex, including poly-N-acetyl-lactosamines with approximately three repeats and proposed I antigen. The four masses observed by β-elimination but not CORA (FIGS. 3B and C) were core 1- and core 2-based glycans lacking terminal sialylation, and therefore were probably biosynthetic intermediates, as might be observed for glycoproteins within an intermediate Golgi compartment before secretion.

To confirm results, the experiments were repeated twice and nearly identical O-glycome profiles were obtained. Electrospray ionization MS was performed and results similar to those from MALDI-MS were obtained. A range of cell types with diverse glycosyltransferases were evaluated (as exemplified by C2GnT1-3) and O-glycome profiles from all the cells were obtained, indicating that Bn-α-GalNAc can access most if not all of the O-glycan machinery. Thus, CORA reflects the cellular O-glycome, which is relatively stable under optimal culture conditions.

Sensitivity of CORA

Figure 4A:
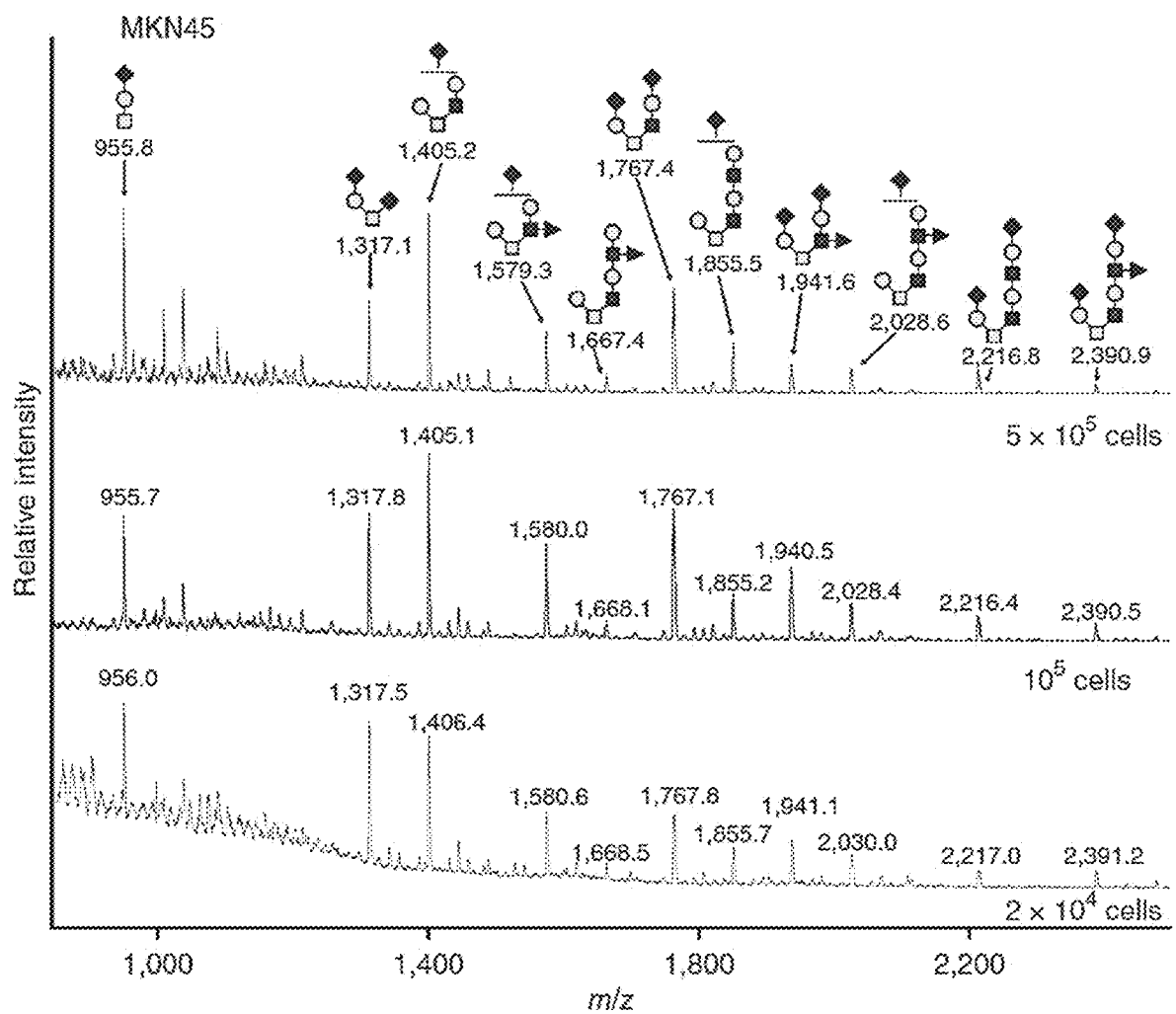
FIG. 4A shows data indicating the sensitivity of CORA. Bn-O-glycans purified from MKN45 seeded at the indicated cell densities and incubated with 50 μM $Ac^3$GalNAc-α-Bn for 3 d. A fraction of total glycans were analyzed by MALDI-MS (composition). Spectra are offset for each seeding density and scaled relative to the maximum intensity. Representative profiles are shown (n=2).
Figure 4B:
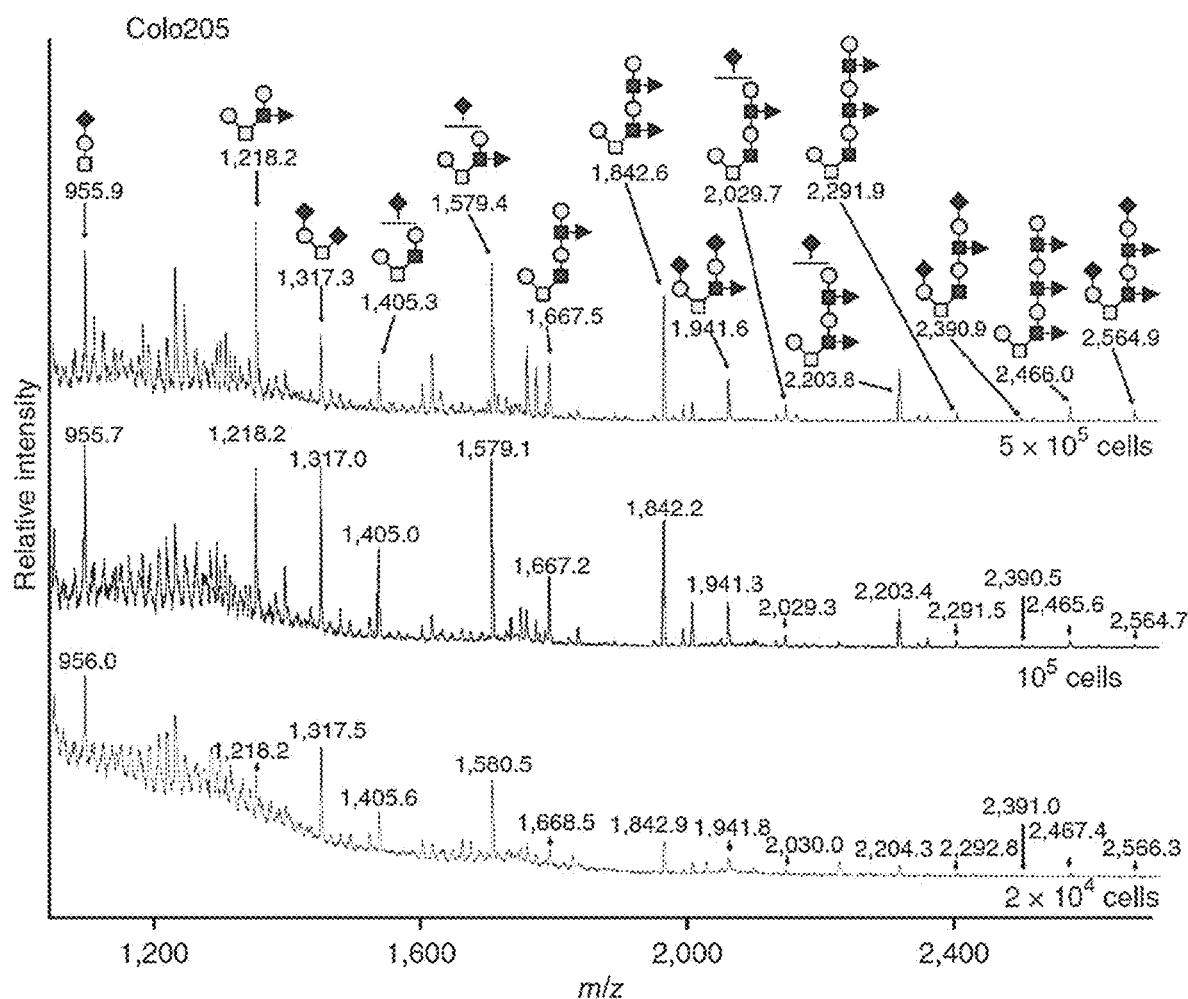
FIG. 4B shows data for Colo205 cells.

The β-elimination used for O-glycan release often requires ≥$10^7$ cells and produces many unassignable peaks. To determine how many cells are needed to get clean, interpretable profiles with CORA, four cell lines were profiled, each seeded at $5\times10^5$, $10^5$ and $2\times10^4$ cells. O-glycomes were obtained from all lines seeded at ≥$10^5$ cells and from three of four lines seeded at $2\times10^4$ cells (FIGS. 4A and B). Notably, profiles did not change with different cell numbers. The detection of Bn-O-glycans from $2\times10^4$ cells cultured for 3 d (to a total of ~$8\times10^4$ cells, assuming ~24-h doubling times) represents an ~100-1,000-fold increase in sensitivity compared to β-elimination.

Profiling the O-Glycomes of Mouse and Human Primary Cells

Because primary cells differ metabolically from cancer cells, CORA was validated on primary human and mouse cells. First immortalized murine pulmonary endothelial cells (mPECs) were profiled with and without Cosmc from Tie2-Cre+; CosmcF/+ mice to determine whether Bn-O-glycan synthesis requires functional Cosmc. Only mPECs with functional Cosmc secreted Bn-O-glycans. Next we isolated Tn– mPECs from mice (Tie2-Cre–; CosmcF/y) and performed CORA. Glycan structures were similar in immortalized and primary mPECs, except for a glycan with the disialyl motif found only in the primary cells. However, the relative abundances of O-glycans differed in these two types of mPECs, suggesting that transformation may alter glycan biosynthesis, as has been demonstrated in human tumors.

Figure 5:
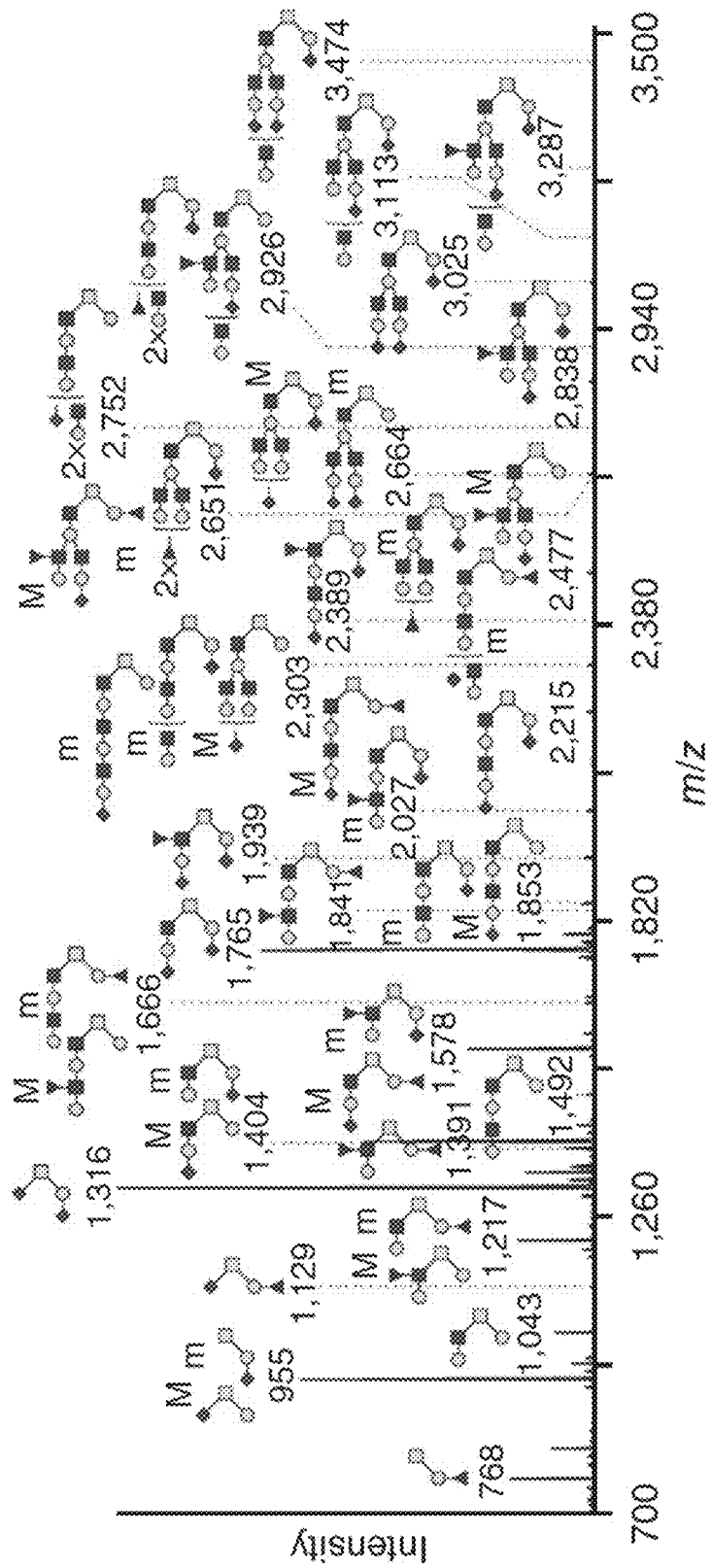
FIG. 5 shows MALDI-TOF-MS/MS profiling of the O-glycome of primary cells. Bn-O-glycans from HUVECs seeded at a density of $12.5\times10^4$ cells, cultured for 2 d and then incubated with 50 μM $Ac_3$GalNAc-α-Bn for 3 more days. Spectra are offset and scaled relative to maximum intensity. Putative structures are based on composition, MS/MS and biosynthetic knowledge.

Primary human dermal fibroblasts and human umbilical vein endothelial cells (HUVECs) were evaluated (FIG. 5).

HUVECs produced 43 O-glycan structures, including those containing poly-N-acetyl-lactosamine, Lewis structures, blood group antigens and I antigen, as confirmed by MS/MS (FIG. 5). Fibroblasts also produced at least 18 glycans (with different masses), including poly-N-acetyl-lactosamine, Lewis structures and blood group antigens. The remarkable diversity of O-glycans in these cells indicates their potential importance.

CORA Promotes the Discovery of Novel Glycans

MS/MS sequencing is needed for definitive determination of glycan structure. However, this is often not possible for glycans derived by β-elimination because of insufficient material. Using CORA, MS/MS sequencing was performed on HL-60 cells, WEHI-3 cells and HUVECs and many diverse glycans were observed (11 for HL-60 cells, 40 for WEHI-3 cells and 43 for HUVECs) as well as novel and unexpected O-glycans, including extended core 1 (HL-60 cells), VIM-2 (HL-60 cells and HUVECs), disialic acid (WEHI-3 cells) and I antigen (WEHI-3 cells and HUVECs) (FIGS. 3A and B and 5).

The I antigen replaces i antigen on red blood cells after embryogenesis but has not been identified on O-glycans from other cell lineages previously, except in secretions. The discovery of I antigen on O-glycans from two distinct non-red blood cell lineages suggests that this may be a common yet unappreciated structure. I antigen has not been observed on O-glycans from these cell lines before. In general, the amounts of O-glycans released by β-elimination are insufficient for the identification of larger O-glycans in the high-mass range, and when larger O-glycans are identified, MS/MS usually is not feasible. CORA permits analyses of small numbers of cells because the cells continuously produce more Bn-O-glycans, thereby amplifying their O-glycomes.

Administration of Compound.

$Ac_3$GalNAc-α-Bn or Bn-α-GalNAc was dissolved to 50 or 100 mM in DMSO and further diluted to 5-250 μM in complete media with 5% (vol/vol) FBS, except for HUVEC and human dermal fibroblast cultures, which were incubated in ATCC preformulated media. Media with compound was administered 1 d (most cells) or 2 d (HUVECs and human dermal fibroblasts) after seeding. Cells were then incubated for 2-4 d with compound before media was collected.

Glycan Purification from Media.

Compound was added to complete media, and media was collected after incubation with cells. Media was run over a 10-kDa centrifugal filter (Amicon Ultra 4, Millipore) for ~30 min at 2,465 g, and flow-through was collected. Bn-O-glycans were subsequently purified from flow-through with a Sep-Pak 3-cc C18 cartridge (Waters) by gravity chromatography. The column was equilibrated by two washes with 2 ml of acetonitrile and four washes with 2 ml of 0.1% (vol/vol) trifluoracetic acid (TFA). Media was applied and the column was washed four times with 2 ml of 0.1% (vol/vol) TFA for each wash. Bn-O-glycans were then eluted with two 1.5-ml applications of 50% (vol/vol) acetonitrile, 0.1% (vol/vol) TFA. Eluent was divided into three fractions, concentrated by CentriVap to remove organic solvents, and lyophilized.

Permethylation and Glycan Analysis.

Dried samples were permethylated. NaOH-DMSO (200 μl) slurry was added followed by 200 μl of methyl iodide to samples. Samples were shaken for 30 min and then spun down at 5,000 g for 5 min. Supernatant was collected and chloroform extraction was performed to isolate permethylated glycans. Chloroform (500 μl) and 500 μl of water was added to supernatant. The samples were mixed and centrifuged at 5,000 g for 1 min. Two more washes were performed with 500 μl of water each before evaporating chloroform by CentriVap for 30 min. Bn-O-glycans were then resuspended in 25 or 50 μl of 50% (vol/vol) methanol. Spotted: 0.5 μl of matrix (10 mg/ml 2,5-dihydrobenzoic acid (Sigma), 50% (vol/vol) acetonitrile, 0.1% (vol/vol) TFA) and 0.5 μl of sample on an Anchorchip target plate, air dried the spots and analyzed by MALDI-TOF-MS using an Ultraflex-II TOF-TOF system (Bruker Daltonics). Peak masses were identified and assigned structures on the basis of composition and knowledge of glycan biosynthetic pathways, or by MS/MS where indicated.

Lectin Blots.

Biotin-labeled *Sambucus nigra* (SNA, B-1305), *Ricinus communis* agglutinin I (RCA-I, B-1085) and *Maackia amurensis* I (MAL-I, B-1315) lectins were purchased from Vector, and horseradish peroxidase (HRP)-labeled peanut agglutinin (PNA, L7759) lectin was purchased from Sigma. Cells were treated with 50 μM $Ac_3$GalNAc-α-Bn or DMSO for 3 d and then harvested and lysed by vortexing of the cell pellet in lysis buffer (0.5% (vol/vol) Triton X-100 in Tris-buffered saline (TBS) supplemented with protease inhibitor tablet (Roche)) once per 5 min for 20 min over ice. Supernatant was collected after centrifugation at 16,000 g for 15 min at 4° C. Protein concentration was determined by BCA (Thermo Scientific) according to the manufacturer's instructions. Lysates were divided into two fractions, and one fraction was treated with 1 μl of neuraminidase (Roche) per 100 μg of lysate at 37° C. overnight. Fetuin (Sigma) was used as a control for lectin staining and enzymatic treatment. Lysates were then boiled in reducing SDS buffer, run on 4-20% Mini-PROTEAN-TGX gels (Bio-Rad) in Tris-glycine-SDS running buffer, and transferred via the Trans-Blot Turbo (Bio-Rad) semi-dry system to nitrocellulose. Membranes were rinsed and blocked with BSA and Tween-20 in essential buffer (25 mM Tris-HCl, 1 mM $CaCl_2$, 1 mM $MgCl_2$, 0.15 M NaCl, pH 7.0) (SNA, RCA-I, MAL-I) or TBS (PNA) for 1 h. Blocking buffer included 0.5% (wt/vol) BSA, 0.5% (vol/vol) Tween-20 for SNA and RCA-I; 0.2% (wt/vol) BSA, 0.2% (vol/vol) Tween-20 for MAL-I; and 5% (wt/vol) BSA, 0.05% (vol/vol) Tween-20 for PNA. PNA-HRP was incubated at 1:1,000 for 1 h at room temperature in blocking solution, and biotin-labeled SNA, RCA-I and MAL-I were incubated in essential buffer at 1, 0.2 and 1 μg/ml, respectively, for 1 h at room temperature or overnight at 4° C. Blots were washed three times for 15 min with TBS mixed with Tween-20 (TTBS) (PNA) or wash buffer (essential buffer, 0.1% (vol/vol) Tween-20 for SNA, RCA-I and MAL-I). Enhanced chemiluminescence reagent (ECL) was immediately added to PNA-HRP, and films were exposed. Biotin-labeled lectins were then incubated for 1 h with 1:5,000 streptavidin-HRP (Vector, SA5004) at room temperature in blocking buffer, washed three times with wash buffer and once with essential buffer (15 min each wash), incubated with ECL and exposed. Blots were stripped with 25 mM glycine, 1% (wt/vol) SDS, pH 2, at room temperature for 30 min and then rinsed twice with PBS for 10 min each time before β-actin staining. Blots were reblocked with 5% (wt/vol) milk and TTBS (0.05% (vol/vol)) for 1 h at room temperature, washed for 5 min with TTBS and incubated with 1:3,000 anti-β-actin (Santa Cruz Biotechnology, sc-47778) in block overnight. Blots were then washed four times (5 min each time) with TTBS and incubated with 1:3,000 HRP-labeled secondary antibody at room temperature for 45 min. Blots were then washed four times (5 min each time) with TTBS, incubated with ECL and exposed.

The invention claimed is:

1. A method of creating and analyzing a library of oligosaccharides comprising,
   (i) providing an acetylated tagged oxygen linked saccharide, wherein the acetylated tagged oxygen linked saccharide is benzyl 2-acetamido-3,4,6-tri-O-acetyl-2-deoxy-α-D-galactopyranoside;
   (ii) mixing the acetylated tagged oxygen linked saccharide with a living in vitro cell at a concentration of less than 250 micromolar (μM) under conditions such that the acetylated tagged oxygen linked saccharide penetrates into the living in vitro cell, and under conditions such that the acetylated tagged oxygen linked saccharide is converted into multiple tagged oxygen linked oligosaccharides within an incubation time of three (3) days;
   (iii) obtaining the multiple tagged oxygen linked oligosaccharides that are secreted from the living in vitro cell or that are present in a cellular cytosol of the living in vitro cell;
   (iv) separating the multiple tagged oxygen linked oligosaccharides to provide the library of oligosaccharides comprising purified individual tagged oxygen linked oligosaccharides; and
   (v) analyzing the purified individual tagged oxygen linked oligosaccharides by mass spectroscopy to provide measured molecular weights of the purified individual tagged oxygen linked oligosaccharides to provide an O-glycome profile.

2. The method of claim 1, wherein the multiple tagged oxygen linked oligosaccharides are secreted from the living in vitro cell.

3. The method of claim 1, further comprising the step of permethylating the multiple tagged oxygen linked oligosaccharides.

4. The method of claim 1, wherein separating the multiple tagged oxygen linked oligosaccharides comprises chromatography or high-pressure liquid chromatography to provide purified individual tagged oxygen linked oligosaccharides.

5. The method of claim 1, further comprising predicting a structure for each of the purified individual tagged oxygen linked oligosaccharides based on the measured molecular weights.

6. The method of claim 1, wherein the purified individual tagged oxygen linked oligosaccharides are immobilized on a solid surface in discrete locations.

7. The method of claim 1, wherein mixing the acetylated tagged oxygen linked saccharide with the living in vitro cell at a concentration of less than 250 μM is at a concentration of 50 μM.

* * * * *